United States Patent [19]

Weischedel

[11] Patent Number: 4,659,991
[45] Date of Patent: Apr. 21, 1987

[54] METHOD AND APPARATUS FOR MAGNETICALLY INSPECTING ELONGATED OBJECTS FOR STRUCTURAL DEFECTS

[75] Inventor: Herbert R. Weischedel, South Windsor, Conn.

[73] Assignee: NDT Technologies, Inc., South Windsor, Conn.

[21] Appl. No.: 480,883

[22] Filed: Mar. 31, 1983

[51] Int. Cl.[4] .................. G01N 27/82; G01R 33/12
[52] U.S. Cl. ..................................... 324/241; 324/262
[58] Field of Search ................ 324/232, 233–242, 324/262, 228–231, 260, 222

[56] References Cited

U.S. PATENT DOCUMENTS

| | | | |
|---|---|---|---|
| 2,245,568 | 6/1941 | Caufield | 324/234 |
| 3,271,664 | 9/1966 | Mountz et al. | 324/232 X |
| 3,424,976 | 1/1969 | Jozewski et al. | 324/225 |
| 3,504,276 | 3/1970 | Proctor et al. | 324/260 |
| 3,535,624 | 10/1970 | Wood | 324/226 |
| 3,739,261 | 6/1973 | Renken, Jr. | 324/232 |
| 4,096,437 | 6/1978 | Kitzinger et al. | 324/227 |
| 4,331,919 | 5/1982 | Beckley | 324/240 X |
| 4,388,593 | 6/1983 | Mittleman | 324/262 |
| 4,495,465 | 1/1985 | Tomaiuolo et al. | 324/232 |
| 4,546,316 | 10/1985 | Lang | 324/262 |

FOREIGN PATENT DOCUMENTS

| | | | |
|---|---|---|---|
| 2932250 | 2/1981 | Fed. Rep. of Germany | 324/222 |
| 0063755 | 5/1980 | Japan | 324/238 |
| 0063757 | 5/1980 | Japan | 324/238 |
| 0071943 | 5/1980 | Japan | 324/238 |
| 913780 | 12/1962 | United Kingdom | 324/229 |
| 1427703 | 3/1976 | United Kingdom | 324/222 |

OTHER PUBLICATIONS

Meltzer et al, "New Method for Steel Cable Testing Developed at NTH", Bergverks-Nytt, 7-8/1969, pp. 13–17.

Primary Examiner—Reinhard J. Eisenzopf
Assistant Examiner—Warren S. Edmonds
Attorney, Agent, or Firm—McCormick, Paulding & Huber

[57] ABSTRACT

A magnetic device for nondestructively inspecting elongated objects such as wire cables and the like, for loss of metallic cross-section due to abrasion and corrosion and internal defects has magnets which induce a saturated magnetic field axially through a short section of the cable as the device and the cable move relative to one another. A sensing coil located in close proximity to the cable between the magnetic field poles detects small changes in leakage flux at the surface of the cable in the saturated condition. The sensed flux changes are applied to an integrator to measure the net variation in flux and correspondingly the total change in cross section. Multiple sense coils mounted on core pieces conforming to the external surface of the cable ensure complete continuity of the inspection process and allow the magnetic device to be installed and removed at intermediate stations along the cable.

18 Claims, 8 Drawing Figures

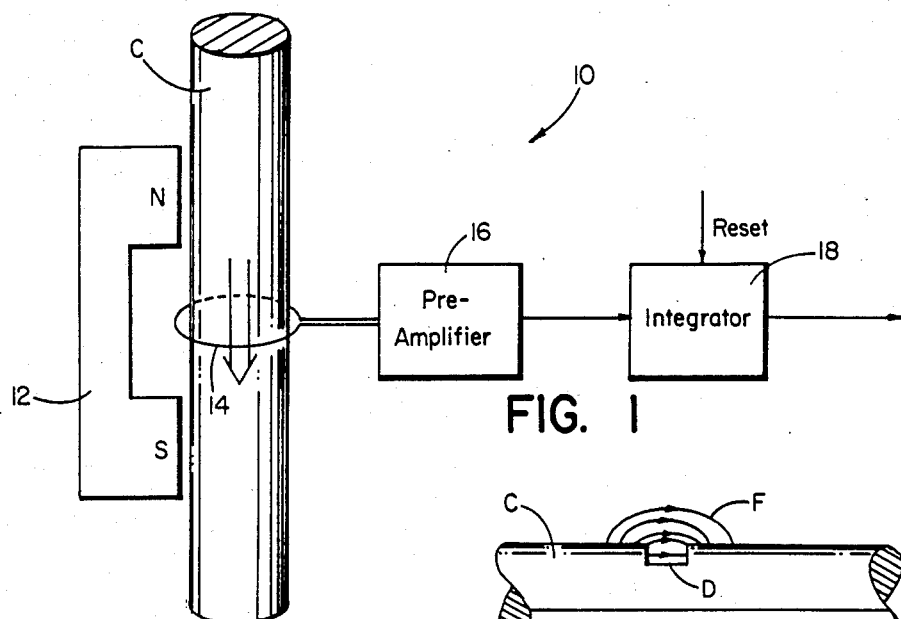
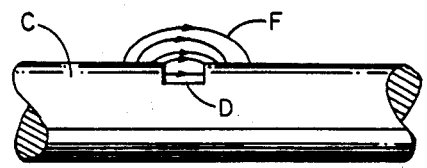
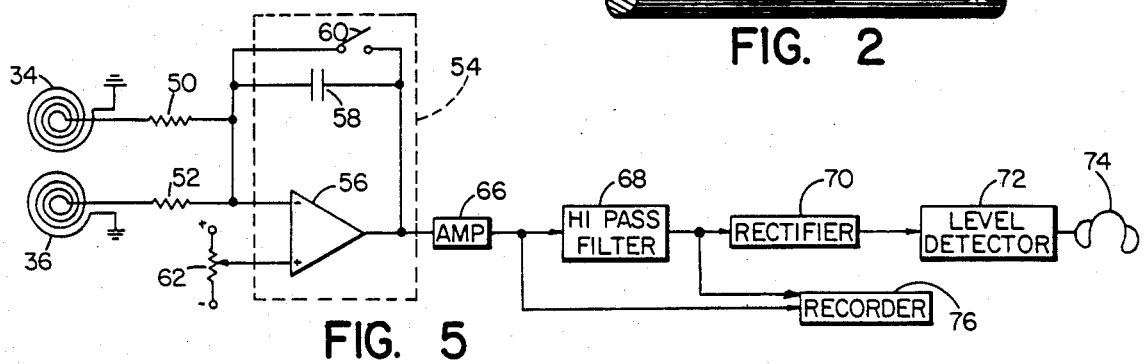
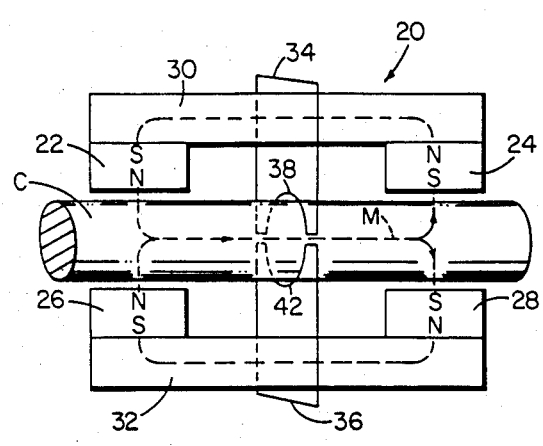
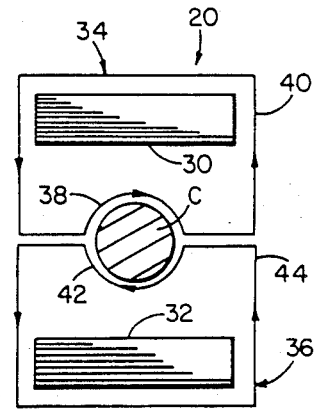

METHOD AND APPARATUS FOR MAGNETICALLY INSPECTING ELONGATED OBJECTS FOR STRUCTURAL DEFECTS

BACKGROUND OF THE INVENTION

The present invention relates to nondestructive testing and evaluation of elongated objects such as wire cables, rods, pipes, and the like, and is concerned more particularly with a magnetic testing method and device for detecting loss in metallic cross section in the objects due to distributed or localized defects on the surface or within the object. The invention may be utilized both at the manufacturing level or in the field.

Reliable and rational techniques for assessing the condition of wire cabling, rods, pipes, and similar elongated ferromagnetic objects is not presently available. Both visual and electromagnetic inspection are known in the art, but depend extensively on the experience and intuition of the human inspector. Serious accidents, various non-scheduled equipment downtimes, and premature replacement as precautionary measures are all consequences of this state of the art, quite apart from the costs involved in the inspection process. Accordingly, it is desirable to provide a reliable technique for testing and measuring the actual strength and remaining life in the metallic objects.

One of the primary problems in the prior art magnetic inspecting devices is the bulk and weight of most instruments. Both of these factors limit the applications of the devices and reduce the resolution of the signals that are generated. Test signals are very complex and are frequently accompanied by high levels of noise due to nonhomogeneities and the coarse construction of objects under test. As a result, data interpretation often is a mixed product of both art and science. Considerable skill is required for operation of the instruments, and the instruments become rather expensive in proportion to their size.

The inspection process addresses two general types of flaws that are observed especially in wire cables. The first is a localized defect, such as a broken wire within the cabling, and the second is a distributed defect such as the loss of metallic cross section due to corrosion or abrasion. Both of these defects cause a reduction in metallic cross section and, consequently, affect cable life and strength.

There are several methods of magnetically testing elongated objects such as cables for localized or distributed defects. One of these methods is designated the main flux method and measures the amount of flux that can be carried by the cable between two longitudinally spaced stations. Since the total flux is directly related to the metallic cross sectional area of the object, measurements of the change in flux can be used to detect and measure the loss of area. U.S. Pat. No. 4,096,437 discloses a specific testing device of this type and includes Hall effect devices for measuring the amount of flux in the region of magnetic poles located at the spaced longitudinal stations along a cable. Changes in cross sectional area caused by corrosion and abrasion can be measured in absolute terms and relative movement of the cable with respect to the measuring device does not enter into the test parameters. One of the disadvantages, however, is that an extended section of the cable is inspected at any given moment. Therefore, only the average value of the metallic cross sectional area is measured with a considerable loss of resolution. Also, small flaws, such as those caused by broken wires or clusters of wires, and other localized defects cannot be detected.

Another method of testing employs a saturated magnetic field extending axially through a section of cabling under test and measures changes in leakage flux due to disruptions or breaks in the rope at the surface of the cable. Flux sensors, such as Hall effect sensors or coils, may measure the changes as the sensor and cable are moved relative to one another, and the test signals derived from the sensors may be displayed on a stripchart recorder that is driven in synchronism with the relative movement of the sensor and cable. U.S. Pat. No. 3,424,976 and U.S. Pat. No. 4,096,437 disclose specific examples of leakage flux detectors.

The advantages of leakage flux systems are that small external and internal flaws, such as broken wires, can be detected and a qualitative indication of corrosion and abrasion is also available. The disadvantages of the prior art sensors are that the reduction in cross sectional area caused by abrasion and corrosion cannot be determined quantitatively, and since the measurements are representative of changes in the leakage flux, signal amplitudes for coils are proportional to the test speeds. As a result of the latter, tachometers are generally used in connection with an automatic gain control circuit to equalize the signals for recording purposes. This adds complexity and weight to the instruments, and additionally, a certain minimum speed is generally required for a threshold signal. Because of the nonhomogeneous structure of wire cabling, test signals are very noisy, and the noise signal cannot be removed by filtering because the differences in the levels of the noise and flaw signals are very small. Still further, because of the requirement for movement between the magnetic device and the cable, the process cannot be carried out at the ends of a cable which is permanently secured in place.

Accordingly, it is a general object of the present invention to provide a method and apparatus for quantitatively determining the loss of metallic cross section caused by corrosion, abrasion, and other factors, and to also obtain at least a qualitative measurement of localized defects without the disadvantages mentioned above.

SUMMARY OF THE INVENTION

The present invention resides in a magnetic inspection method and device for nondestructively detecting loss in cross sectional area and localized defects in elongated, magnetically permeable objects such as wire, cables, rods, pipes, and the like.

The device, which carries out the method, is comprised of magnetic means having two opposite magnetic poles that are spaced from one another for positioning at longitudinal stations along the object. The magnetic means induces magnetic flux in the object between the stations at a saturation level so that changes in the leakage flux at the surface of the object manifest the changes in cross section. The magnetic means also provides a ferromagnetic flux return path for completing the flux circuit between the poles.

A flux detector means for measuring the changes in leakage flux has a sensing coil that is interlaced with a substantial portion of the flux circuit through the object and the return path of the magnetic means. The sensing coil has a portion located adjacent the exterior surface of the object between the magnetic poles for sensing perturbations in leakage flux. These perturbations, as explained above, are caused by the changes in metallic cross section brought about either through distributed defects, such as corrosion or abrasion, or by local defects, such as fractures at the surface or within the object.

The changes in leakage flux sensed by the coil are manifested in voltages induced in the coil, and in order to obtain a quantitative measure of the changes, integrating means are connected to the coil and produce a signal representative of the total change of flux from a selected reference point along the object. Since the magnetic flux field saturates the portion of the object between the magnetic poles, the total change in flux represents the total change in cross section.

Therefore, the magnetic device provides a quantitative measure of the change in metallic cross section caused by abrasion and corrosion. Localized defects, such as broken wires, also influence the leakage flux, and are detected at a qualitative level. The integration of the flux changes renders the signal output by the device independent of the speed of relative movement between the device and the inspected object, and suppresses noise in the output due to nonhomogeneities of the object.

BRIEF DESCRIPTION OF THE DRAWINGS

FIG. 1 is a schematic illustration of a magnetic inspection device in accordance with the present invention for detecting loss of metallic cross section in an elongated object, such as a wire cable.

FIG. 2 is a schematic illustration of leakage flux that exists on the exterior surface of a magnetically saturated wire cable in the vicinity of a flaw in the cable.

FIG. 3 schematically illustrates a preferred embodiment of the magnetic inspection device along a longitudinal section of a cable.

FIG. 4 is a schematic view of the magnetic device as viewed along the axis of the cable in FIG. 3.

FIG. 5 is an electrical diagram of detection circuitry employed with the magnetic device shown in FIGS. 3 and 4.

DESCRIPTION OF PREFERRED EMBODIMENTS

Figure 6:
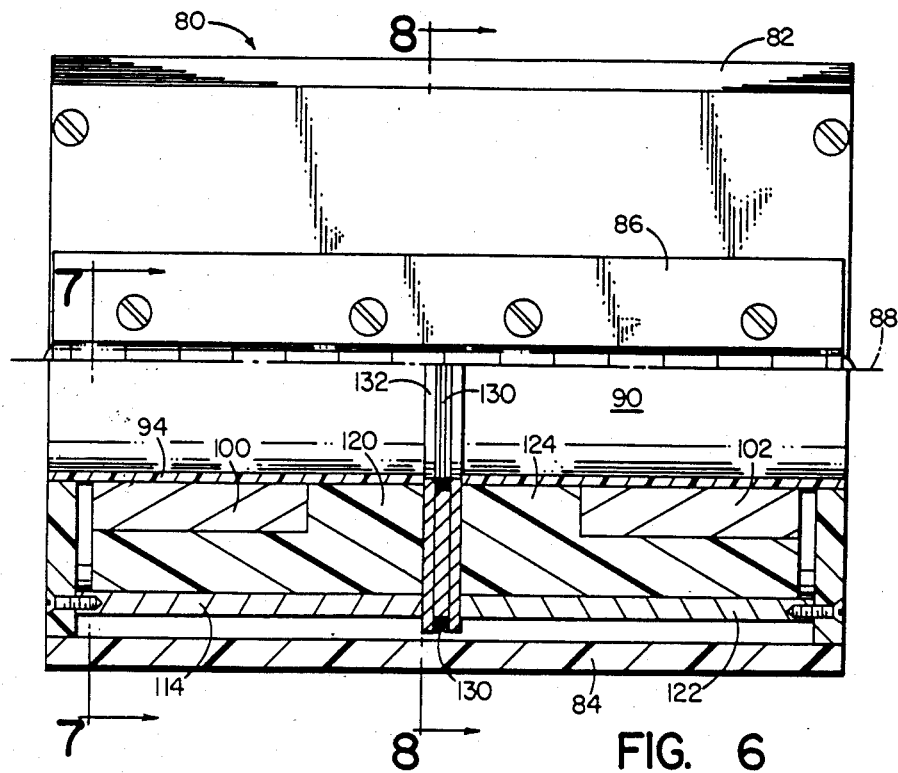
FIG. 6 is another embodiment of the magnetic device partially in section and shows the detailed construction of the device in an elevation view.

FIG. 1 illustrates a magnetic inspection device 10 for nondestructively detecting loss of metallic cross section in a wire cable C. Loss in metallic cross section can occur due to abrasion through use, corrosion, and also due to local defects such as fractures or breakage of individual wires on the exterior surface of the cable or internally. The magnetic device 10 may be used to inspect cables, either in the manufacturing process or in a working environment without removing the cable C from its normal operating position. The magnetic device may also be used for inspecting other types of elongated, magnetically permeable objects, such as rods, bars, billets, pipes, and the like.

The magnetic device 10 is comprised of magnet means for inducing a saturated magnetic field axially through the cable C in the longitudinal direction. The means illustrated for this purpose in FIG. 1 is a permanent magnet 12 having north and south poles located at spaced longitudinal stations along the cable.

A sensing coil 14 is located at a position midway between the poles of the magnet 12 and lies in a plane perpendicular to the longitudinal axis of the cable C with the sensing axis aligned with the longitudinal axis. The coil 14 circumscribes substantially the entire circumference of the cable in close proximity to the exterior surface and detects changes in leakage flux as the cable and the device move relative to one another in the longitudinal direction. Relative movement may be produced in a variety of manners. In installations where the cable is normally moved, such as in cranes, elevators, mine hoists, aircraft control linkages, and cable cars, the device is normally mounted in a stationary position, and the cable is pulled through the device. In other installations where the cable is normally stationary, such as guy lines, suspension cables, and the like, the instrument may be moved along the cable.

FIG. 2 illustrates the local perturbations in leakage flux that are created where a reduction or loss in the metallic cross section of the cable exists. Since the magnetic device induces a saturated field in the cable, any reduction in cross section due to a defect D forces the lines of flux out of the cable and produces a local perturbation that can be detected through sensing coil as the lines of flux cut back and forth through the coil. The radial location of the local defect, either at the core of the cable or at its exterior surface, produces the same effect and only influences the strength of the signal that is sensed. The azimuthal location of the local defect also causes the leakage flux to be more prominent on one part of the exterior surface than another, and in order to ensure that all defects are detected regardless of location, the sense coil preferably circumscribes substantially the full periphery of the cable at the station intermediate the poles of magnet 12. Gradual changes in the metallic cross section due to corrosion or abrasion also produce changes in the leakage flux in essentially the same manner over a longer section of the coil. Such changes also are detected through the sensing coil at a lower signal level due to a less rapid change in the leakage flux pattern.

In FIG. 1, the voltage signals induced in the sense coil 14 by the leakage flux changes are strengthened in pre-amplifier 16 and then processed through an integrator 18 in accordance with one aspect of the present invention. It should be understood that the flux changes observed by the sense coil 14 are caused by the change of metallic cross section of the cable and the magnitudes of the signals induced in the coil are related to the change in cross section. Integration of the signals along the cable thus represents the total change of metallic cross section from the reference station where the integration started to the transverse plane of the cable in which the sense coil 14 is located. The integrator 18 can be reset as shown and as desired for measuring the loss of metallic cross section in different sections of the cable. Hence an accurate measure of the loss of metallic cross section can be achieved, and additionally, an accurate location of a local defect is obtained for subsequent repair or replacement.

The advantages of the magnetic device 10 are several. The output signal from the integrator 18 yields a signal that represents the loss of metallic cross section in absolute terms and it provides a quantitative measure of that loss. The factor of cable speed does affect the signal output since the integrated sum represents the total change in flux regardless of the rate at which the change is measured. The integration also suppresses noise, which is substantial in the output signal from the coil, and thus improves the signal to noise ratio at the output.

The apparatus illustrated in FIG. 1 has a single continuous coil 14 that substantially circumscribes the wire cable C. Since the coil customarily has many windings or turns in order to generate a voltage signal in the milli-volt range, the coil cannot be mounted on or removed from the cable except at the cable ends. This limitation is impractical in many situations, and consequently another embodiment of the invention is shown schematically in FIGS. 3 and 4.

In FIG. 3, a magnetic device 20 is shown with a set of permanent magnets 22, 24 disposed along one lateral side of the cable C and another set 26, 28 at the opposite side. The magnets 22, 24 are interconnected by a ferromagnetic bar 30 to provide a magnetic flux return path between the magnets for the magnetic flux M that is induced in the cable, as illustrated by the dotted lines. In a similar manner, a ferromagnetic bar 32 interconnects the permanent magnets 26, 28. In this embodiment, the magnets themselves form the pole pieces to generate the flux M in the cable at a saturation level.

Two sensing coils 34, 36 are located in a transverse plane between the respective sets of magnetic poles. The coil 34 has one portion 38 located in close proximity to the exterior surface of the cable for detecting perturbations in leakage flux at one side of the cable, as explained above in connection with FIGS. 1 and 2. Another portion 40 of the coil extends around the outside of and circumscribes the return flux path through the bar 30 as shown most clearly in FIG. 4. Similarly, the coil 36 has one portion 42 located adjacent the coil C at one side of the cable and another portion 44 that extends around the flux return path through the bar 32.

It can be shown that the coils 34, 36 are collectively equivalent to the coil 14 in FIG. 1 for detecting changes in leakage flux at the exterior surface of cable C. The equivalency arises due to the fact that the portions 38, 42 lie adjacent the exterior cable surface in the same manner as the coil 14, and the portions 40, 44 collectively circumscribe substantially the entire flux circuit and effectively are not influenced by the changes of flux within that circuit. It will be observed that with this configuration, each of the coils 34, 36 is interlaced with a substantial portion of the flux circuit through the object
and the return paths. Limited amounts of leakage flux through the air outside of the coils will not materially influence the leakage flux signal induced in the coils.

With the separate coils 34, 36 in the magnetic device 20, the device can be manufactured with two separable housing portions for mounting and demounting the device on an elongated object at any station intermediate its ends. It is not essential to have multiple poles and magnets as shown; however, the symmetric construction assures a uniform flux density in the field through the cable and permits operation of the device at the saturation level to be achieved with greater certainty. With particularly large cables, multiple sets of magnets are more manageable and preferable.

FIG. 5 illustrates the electrical schematic for coupling the two coils 34, 36 to detection circuitry, as defined generally in FIG. 1. Each coil 34, 36 is comprised of multiple turns, and the ends are poled and electrically connected as shown in FIG. 5, so that the output voltages are additive. In other words, a loss of metallic cross section in the cable at the plane of the coils produces two voltages, and those voltages are added in order to obtain a maximum signal representative of the leakage flux perturbations.

The voltage signals are added through resistors 50, 52 at the input of an integrator 54. The integrator is comprised by a differential, operational amplifier 56, feedback capacitor 58, and a reset switch 60. The voltage signals are applied to the negative input of the amplifier, and a voltage from a trimming potentiometer 62 is applied to the positive input to balance the coil inputs at the noise level of the voltage from the coils. Thus the integrator produces an output signal that is representative of the net loss of metallic cross section along the cable between a reference station at which the switch 60 was initially opened and a station where the coils are eventually moved. Preferably the integrator should have a high degree of stability, and one integrator found suitable for this purpose is model OP27 manufactured by Precision Monolithics, Inc. of Santa Clara, Calif.

The output of the integrator 54 is processed through an amplifier 56 and a high pass filter 68 to a rectifier 70 or a recorder 76. The high pass filter 68 effectively removes any DC component of the signal and permits the rectifier to be operated at a higher gain. The rectifier is utilized to condition the signals for audio annunciators that provide a qualitative indication of flaws in the cable as the inspection process is carried out. For this purpose, the rectifier signal is processed through level detector 72 which passes only signals above a predetermined level, and such signals are used to drive the headphones 74.

For a quantitative analysis of the integrated signal in both filtered and unfiltered form, a multi-channel recorder 76 is connected to the input and to the output of the highpass filter 68. If the recorder is a stripchart recorder that is run at a speed proportional to the motion between the magnetic device and the cable, the positions of the various defects on the stripchart can be correlated with their locations in the cable.

Figure 7:
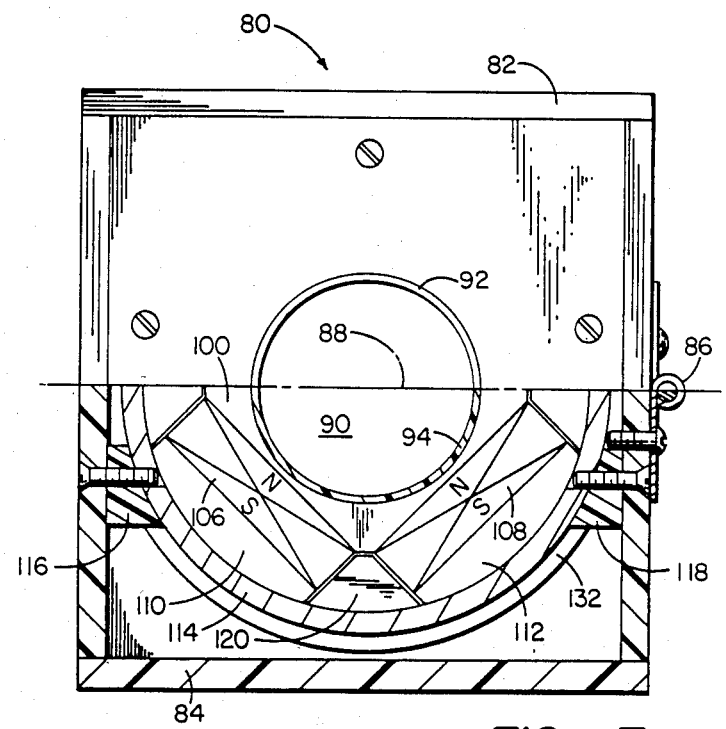
FIG. 7 is a partially sectioned end view of the device in FIG. 6 and shows the internal structure along the sectioning line 7—7.
Figure 8:
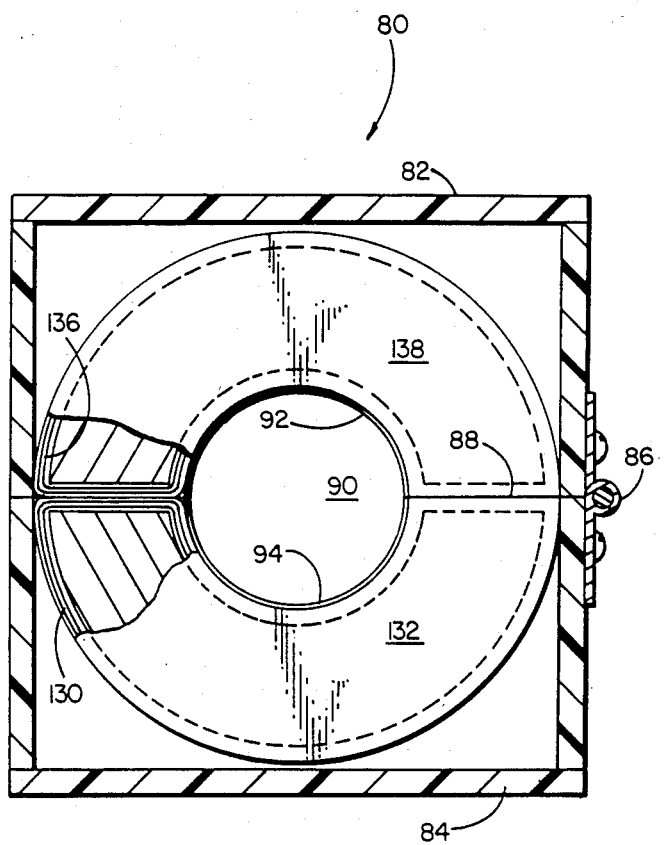
FIG. 8 is a cross sectional view of the device in FIG. 6 as seen along the sectioning line 8—8 with portions of the core pieces broken away.

FIGS. 6–8 disclose the structural details of a further magnetic device, generally designated 80, which utilizes sensing coils interlaced with the flux circuit in the same manner as illustrated in FIGS. 3 and 4.

The magnetic device 80 has an exterior housing 82 made from a nonmagnetic material, such as acrylic plastic, and is divided into an upper housing part 82 and a lower housing part 84. The two housing parts are connected together by means of a piano hinge 86 along one side, so that the parts can be opened and closed for mounting on a cable or other elongated object. For this purpose, the parts 82 and 84 also define an open central passageway 90 through which a cable may move. The passageway is lined by semicircular sleeves 92, 94 which are made from a material, such as a tetrofluoroethylene plastic. The plastic sleeves serve as a low-friction guide for the cable through the housing and may be replaced from time to time due to wear.

Mounted at one axial end of the housing, adjacent the passageway 90, is a pole piece 100 as shown most clearly in FIGS. 6 and 7. A similar pole piece 102 is mounted at the opposite end of the passageway. In FIG. 7, the pole piece 100 has a generally triangular configuration with a semi-circular groove that conforms to the circular passageway 90 and positions the pole piece in close peripheral relationship with the exterior surface of a cable within the passageway.

Permanent magnets 106 and 108 are mounted in contacting relationship with the two sides of the pole piece 100 at 45 degrees to the parting plane of the housing as in FIG. 7. Both magnets are polarized radially relative to the central passageway and have their north poles positioned in contacting relationship with the pole piece 100. A similar set of magnets mate with the pole piece 102 at the opposite end of the passageway with the polarities reversed from that shown in FIG. 7 so that the pole pieces 102, 104 may induce a saturated field through the section of cabling that lies within the passageway 90 during the inspection process. The magnets 106, 108 are supported against the pole piece 100 by means of steel pedestals 110 and 112 respectively, and by a semi-cylindrical, steel sleeve 114 which is supported in the lower housing part 84 by struts 116, 118. A molded plastic filler 120 holds the magnets and the pedestals and the pole piece 100 securely in position within the semi-circular steel sleeve 114, as shown in FIGS. 6 and 7.

The magnets, pedestals, and pole piece 102 are similarly supported at the opposite end of the passageway 90 by means of a semi-cylindrical steel sleeve 122 and a plastic filler 124. Due to the symmetry of construction, complete details as in FIG. 7 are not illustrated.

The construction of the magnetic device 80 in the upper housing part 82 is the same as that in the lower part with similar elements being symmetrically located about the parting plane 88. Accordingly, there are multiple sets of magnets and pole pieces which induce a saturated magnetic field in that section of the cable which extends through the central passageway 90 of the housing. The supporting semi-cylindrical steel sleeves 114, 122 in the lower portion of the housing, and the corresponding sleeves in the upper portion of the housing, comprise the flux return path, so that a complete magnetic circuit through the cable and the semi-cylindrical sleeves exists wholly within the housing.

Mounted at the midstation along the passageway 90 and between the semi-cylindrical sleeves 114, 122 is one sensing coil 130 shown in FIGS. 6 and 8. The sensing coil is mounted generally in a transverse plane perpendicular to the axis of the passageway 90 by means of a ferromagnetic core piece 132. The core piece is a generally planar or flat, plane-like member and has an arcuate configuration with the radially inner portion confronting the cable being semicircular to correspond with the external periphery of a cable. Additionally, the core piece 132 has a peripheral groove which houses the windings of sensing coil 130 and holds the coil in position. A similar coil 136 and a core piece 138 are mounted in the upper housing part 82 and mate with the coil 130 and core piece 132 at the parting plane 88 of the housing.

It will thus be observed in FIG. 8 that when the housing is closed on a cable within the passageway 90, the core pieces 132 and 138 conform to the entire periphery of the cable at its exterior surface and serve as a single planar core that completely circumscribes the passageway at a station midway between the poles of the magnetic field induced in the cable. The outer portion of the coils 130 and 136 lies outside of the flux return path established by the semi-cylindrical sleeves 114, 122 in the bottom portion of the housing and the corresponding sleeves in the top. Furthermore, the portions of the coils 130 and 136 lying adjacent to the cable are influenced by the changes in leakage flux due to the variations in the metallic cross section of the cable and produce a voltage signal corresponding to those changes as explained above.

In summary, applicant has disclosed a magnetic device in several different embodiments for nondestructively testing elongated ferromagnetic objects for loss of metallic cross section. Such losses may be due to local breaks within the object or due to abrasion and corrosion that removes metal from either the interior or exterior surfaces of the object. Although different forms of the device have been illustrated, it should be clear that at least one magnet is required for inducing a saturated magnetic field through the sections of object under test, and at least one sensing coil for detecting changes in leakage flux from that field at the surface of the object. Preferably, the device includes two coils with at least one magnet and a set of poles associated with each coil, so that the device can be mounted or removed from an elongated object at stations intermediate its ends. In its method of operation, the cable is moved through the device while the magnets induce a field in one section of the object. The leakage flux changes at the surface of the object are sensed and then integrated. The integration provides a quantitative meausre of the net change in metallic cross section and eliminates the speed factor from the output of the device.

While the present invention has been described in several preferred embodiments, it will be understood that numerous modifications and substitutions can be had without departing from the spirit of the invention. For example, the specific dimensions shown in the FIGS. 6-8 are merely exemplary of one form of the invention. Different size objects being inspected may require different proportioning for accurate results. It is not essential to use multiple magnets as shown, as long as the magnets employed provide a relatively uniform flux field within the object. Accordingly, the present invention has been described in several preferred embodiments by way of illustration, rather than limitation.

I claim:

1. A magnetic inspection device for nondestructively detecting loss in metallic cross section and localized discontinuities in elongated objects, such as wire cables, rods, pipes, and the like comprising:

magnet means having two opposite magnetic poles spaced from one another for positioning and relative movement adjacent an elongated magnetically permeable object with the poles at longitudinally spaced stations of the object, and for inducing in sections of the object between the stations, magnetic flux at the saturation level, the magnet means also defining a ferromagnetic flux return path between the poles externally of the object for completing the flux circuit; and magnetic flux detector means having a sensing coil interlaced with the flux circuit through the ferromagnetic flux return path at a position between the poles and laterally of the elongated object and circumscribing the portion of the flux circuit in the return path of the magnet means without circumscribing the elongated object and having a sensing portion of the coil located adjacent the exterior surface of the elongated object between the two magnetic poles of the magnetic means for sensing perturbations in leakage flux at the exterior surface caused by defects in the object, as the object and inspection device move relative to one another.

2. A magnetic inspection device for detecting defects as defined in claim 1, wherein:
a magnetically permeable core in the form of a flat, plane-like member is mounted between the poles of the magnet means substantially pependicular to the elongated object; and
the sensing coil of the detecting means is mounted on the core.

3. A magnetic inspection device for detecting defects as defined in claim 2 wherein a portion of the magnetically permeable core confronting the object is shaped to conform to the exterior surface of the object; and the sensing portion of the coil is mounted in a groove of the confronting portion.

4. A magnetic inspection device as in claim 3 wherein the magnetically permeable core has an arcuate configuration.

5. A magnetic inspection device for detecting defects in elongated objects as defined in claim 1 wherein:
the magnetic means has at least two sets of opposite magnetic poles for inducing magnetic flux simultaneously in the same section of the elongated object, one set of opposite magnetic poles being located adjacent a different portion of the exterior object surface than the other set of opposite magnetic poles and separate flux return paths associated respectively with the sets of opposite magnetic poles, and
the magnetic flux detector means has two sensing coils, each coil being interlaced with and circumscribing a different flux return path than the other coil, and having a sensing portion located adjacent an exterior surface portion of the object different from the other coil, both coils being located at the same longitudinal station of the elongated object.

6. A magnetic inspection device for detecting defects as in claim 5, further including:
a housing defining a central passageway through which an elongated object may move longitudinally of itself during inspection, and having two separable housing portions defining a parting plane intersecting the central passageway along its length to permit the housing portions to be mounted in mating relationship over and removed from the elongated object intermediate the ends of the object; and
at least one sensing coil is supported in each separable housing portion.

7. A magnetic inspection device for detecting defects as defined in claim 6 wherein the separable housing portions are connected together by a hinge.

8. A magnetic inspection device for detecting defects as defined in claim 6 wherein:
a magnetically permeable core having a generally planar configuration is divided into two parts, each part being mounted in a respective one of the separable housing portions to mate with the other and form a planar core completely circumscribing and generally perpendicular to the central passageway and elongated objects therein when the separable housing portions are mounted over the object in mating relationship; and
the two sensing coils are mounted respectively on the two parts of the magnetically permeable core.

9. A magnetic inspection device for inspecting elongated magnetically permeable objects, such as wire cables and the like, for abrasion, corrosion, and internal defects, comprising:
magnetic means having two magnetically opposite poles and a connecting ferromagnetic flux return path for movement relative to an elongated magnetically permeable object to be inspected, with the poles longitudinally separated along the object for inducing a saturated magnetic field in the portion of the object between the poles, whereby changes in transverse cross section and internal defects of the object produce detectable changes in leakage flux from the field between the poles at the exterior surface of the object;
a sensing coil disposed between the longitudinally separated poles at one lateral side of the elongated object adjacent the exterior surface of the object and circumscribing the ferromagnetic flux return path of the magnetic means with the sensing axis of the coil aligned with the longitudinal axis of the cable or other elongated object to detect the changes in leakage flux at the exterior surface as the object and magnetic device move relative to one another, which changes generate a voltage signal in the coil representing the variations in flux and corresponding changes in cross section of the object caused by abrasion, corrosion, and local defects; and
integrating means connected to the sensing coil for integrating the voltage signal with time and producing a signal indicative of the total change in flux in the object and corresponding change in cross section.

10. A magnetic device for inspecting elongated magnetically permeable objects as defined in claim 9, wherein: the windings of the sensing coil are located generally in a plane perpendicular to the elongated object and intermediate the two magnetic poles.

11. A magnetic device for inspecting elongated magnetically permeable objects as defined in claim 10 wherein the sensing coil is mounted at one side of the elongated object on a core piece, and the core piece partially circumscribes the object in close proximity to the exterior surface of the object to intercept leakage flux at the surface.

12. A magnetic device for inspecting as defined in claim 11 wherein the core piece has a generally arcuate configuration to conform to generally cylindrical elongated objects, and a peripheral groove; and the sensing coil is mounted in the peripheral groove with one portion of the coil in close proximity to the external surface for sensing changes in leakage flux.

13. A magnetic device for inspecting elongated magnetically permeable objects, such as wire cables and the like, as in claim 9, wherein:
a plurality of said magnet means having magnetically opposite longitudinally separated poles and connecting flux return paths are disposed about the elongated magnetically permeable object and jointly movable relative to the object;
a plurality of said sensing coils are spaced from one another and disposed generally in a single plane about the exterior surface of the object with sensing axes of each aligned parallel with the longitudinal axis of the cable or other elongated object; and
the coils collectively circumscribe all of the flux return paths of the magnet means and are located adjacent different portions of the exterior object surface; and the integrating means is connected with each sensing coil to collectively integrate the changes in leakage flux at the different portions of the exterior surface in said single plane.

14. A magnetic device for inspecting elongated magnetically permeable objects as defined in claim 13 wherein the plurality of sensing coils are shaped and located to sense leakage flux at each portion of the exterior object surface in said single plane.

15. A magnetic device for inspecting elongated magnetically permeable objects as defined in claim 13 wherein:
the plurality of sensing coils are mounted on core pieces and the core pieces collectively circumscribe the entire exterior surface of the object in said single plane for integrating the changes in leakage flux around the entire surface.

16. A magnetic device for inspecting as in claim 13 further including:
a split housing having two separabe portions defining a central passageway for the elongated object along a parting plane between the separable portions; and wherein:
two magnetically opposite poles of one magnetic means of the plurality and a sensing coil are mounted in one of the separable housing portions; and another two magnetically opposite poles of another magnetic means of the plurality and a sensing coil are mounted in the other of the separable housing portions; and
the integrating means is connected with each of the sensing coils in the one and the other of the housing portions.

17. A method for nondestructively inspecting an elongated magnetically permeable object, such as wire cable and the like, for abrasion, corrosion, internal defects, and the like, comprising the steps of:
inducing a magnetic field extending longitudinally through the elongated magnetically permeable object between longitudinally spaced stations at a saturation level to establish leakage flux at the exterior surface of the object, the field being part of a magnetic circuit through the object between the spaced stations, the circuit being closed externally of the object by a ferromagnetic flux return path;
moving the magnetic field and spaced stations progressively and longitudinally along the object, and sensing the changes in leakage flux at the exterior surface of the object due to the changes in metallic cross section of the object by means of a sensing coil disposed at one side of the elongated object, interlaced with the closed magnetic circuit and circumscribing the portion of the circuit in the ferromagnetic flux return path externally of the object; and
integrating the changes in leakage flux sensed by the coil to obtain a measure of the total change in flux and corresponding change in cross section along that part of the elongated object through which the magnetic field is moved.

18. A method of inspecting elongated magnetically permeable objects as defined in claim 17, wherein the step of inducing includes closing the magnetic circuit through a plurality of circuit portions disposed externally of the elongated object; and the step of sensing comprises employing a plurality of the sensing coils interlaced with the magnetic circuit and circumscribing the plurality of external circuit portions respectively so that changes in magnetic flux around the full periphery of the object are sensed.

* * * * *